(12) United States Patent
Cvetovich et al.

(10) Patent No.: US 6,486,195 B1
(45) Date of Patent: Nov. 26, 2002

(54) THERMODYNAMICALLY STABLE CRYSTAL FORM OF 4"-DEOXY-4"-EPI-METHYLAMINO AVERMECTIN B1A/B1B BENZOIC ACID SALT AND PROCESSES FOR ITS PREPARATION

(75) Inventors: Raymond Cvetovich, Scotch Plains, NJ (US); James A. McCauley, Belle Mead, NJ (US); Richard Demchak, Langhorne, PA (US); Richard J. Varsolona, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 08/376,318

(22) Filed: Jan. 20, 1995

Related U.S. Application Data

(63) Continuation-in-part of application No. 08/109,189, filed on Aug. 19, 1993, now abandoned.

(51) Int. Cl.[7] .................... A61K 31/352; A61K 31/365; C07D 313/00

(52) U.S. Cl. ........................................ 514/450; 549/264
(58) Field of Search ........................... 549/264; 514/450

(56) References Cited

U.S. PATENT DOCUMENTS 4,935,531 A * 6/1990 Ward et al. .................. 549/264
5,288,710 A * 2/1994 Cvetorich ..................... 514/30

FOREIGN PATENT DOCUMENTS

EP         0 465 121      * 1/1992

* cited by examiner

*Primary Examiner*—Ba K. Trinh
(74) *Attorney, Agent, or Firm*—David L. Rose; Joseph F. DiPrima

(57) ABSTRACT

The most thermodynamically stable crystalline form of the benzoic acid salt of 4"-deoxy-4"-epi-methylamino avermectin B1a/B1b as the hemihydrate is obtained by crystallization from organic solvents containing a controlled amount of water.

4 Claims, No Drawings

THERMODYNAMICALLY STABLE CRYSTAL FORM OF 4"-DEOXY-4"-EPI-METHYLAMINO AVERMECTIN B1A/B1B BENZOIC ACID SALT AND PROCESSES FOR ITS PREPARATION

CROSS REFERENCE TO RELATED APPLICATIONS

This application is a continuation-in-part of application Ser. No. 08/109,189 filed Aug. 19, 1993, now abandoned.

BACKGROUND OF THE INVENTION

The benzoic acid salt of 4"-deoxy-4"-epi-methylamino avermectin B1a/B1b is known and known to be a stable salt as described in European Patent Publication EP 0465121-A1. The added stability relative to the stability of the previously described hydrochloride salt provided much greater shelf life for this important agricultural insecticide.

SUMMARY OF THE INVENTION

This invention is concerned with the most stable of four crystalline forms of the benzoic acid salt of 4"-deoxy-4"-epi-methylamino avermectin B1a/B1b a known agricultural insecticide, and processes for preparing it.

The four crystalline forms that have been identified are designated as forms A, B, C and D, three of which are hydrated (B, C and D). The most thermodynamically stable crystalline form is the hemi-hydrate B. Knowing the most stable crystalline form and devising processes for producing the product in that form is extremely important in that it provides bulk material with crystal homogeneity that is not going to transform to another crystal habit on storage.

The novel crystal form B has been found to be significantly less hygroscopic than the other crystal forms and in addition it retains much less solvent. These attributes provide for a much more stable and uniform form of the final product which is used to prepare agricultural products and pharmaceutical dosage forms.

The novel processes for producing crystal form B comprises crystallization of the compound from an organic solvent containing a controlled amount of water.

DETAILED DESCRIPTION OF THE INVENTION

The novel compound of this invention is crystalline 4"-deoxy-4"-epi-methylamino avermectin B1a/B1b, benzoic acid salt, hemihydrate in substantially pure form.

It has structural formula:

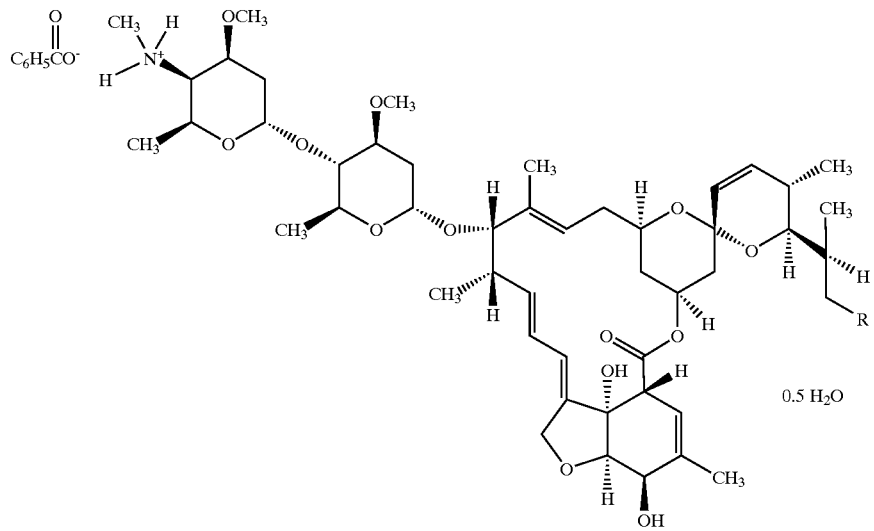

wherein R is —$CH_3$ (B1a) or —H (B1b) and is referred to as Crystal form B, Type B or similar designation.

The differential scanning calorimetry (DSC) curve determined at a heating rate of 20° C./min. under nitrogen flow in an open cup is characterized by a relatively broad water loss endotherm with a peak temperature of 74° C. and a major melting/decomposition endotherm with peak temperature of 155° C., extrapolated onset temperature of 150° C. with an associated heat of 56 Joules/gm. The x-ray powder diffraction pattern for Type B is characterized by d-spacings of 18.13, 9.08, 8.68, 5.03, 4.61, 4.53, 3.97 and 3.82 Å. The aqueous solubility is pH dependent. At pH 5, acetate buffer, it has a solubility of 0.32 mg/ml.

The novel process of this invention comprises recrystallizing the compound in any energetic state from an aqueous organic solvent. Preferably form B is prepared from Form A.

The aqueous organic solvent useful in the novel process is preferably acetonitrile with 2–4% w/w of water; methyl t-butyl ether (MTBE) with 0.5 to 0.8% w/w of water; or isopropanol (IPA) with 0.1–0.3% w/w of water.

Compound of crystal form A, C or D is dissolved in the organic solvent at about 50–60° C. treated with the requisite amount of water, seeded with Type B crystals, cooled to and aged at about 15–30° C. for about 2–4 hours and further cooled to about 5° C. over a period of about 1–2 hours.

The crystalline product is collected on a filter and dried in vacuo.

The utility and methods of use of the benzoic acid salt described herein and the free base thereof are well known by those skilled in the art and fully described in the scientific and patent literature.

It has significant parasiticidal activity as an anthelmintic, ectoparasiticide, insecticide and acaricide, in human and animal health and in agriculture. As an agricultural pesticide it has activity against insect pests of stored grains such as Tribolium sp., Tenebrio sp., and of agricultural plants such as spider mites, (Tetranychus sp.), aphids, (Acyrthiosiphon sp.); against migratory orthopterans such as locusts and immature stages of insects living on plant tissue. The compound is useful as a nematocide for the control of soil nematodes and plant parasites such as Meloidogyne sp. which is of importance in agriculture. The compound is active against other plant pests such as the southern army worm and Mexican bean beetle larvae.

The compounds are applied using known techniques as sprays, dusts, emulsions and the like, to the growing or stored crops to effect protection from such agricultural pests. For the treatment of growing crops, the compound is administered at a rate of about 5–50 gms per hectare. For the protection of stored crops it is normally administered by spraying with a solution containing from 0.1–10 ppm. of the compound.

The following examples are provided in order that the invention might be more fully understood. The examples are not to be construed as limitations upon the scope of the invention.

EXAMPLE 1

5-O-t-Butyldimethylsilyl avermectin B1a/B1b

A solution of 50 g of avermectin B1a/B1b (dried over $P_2O_5$ in high vacuum to constant weight), 24 g of imidazole and 24 g of tert-butyldimethylsilyl chloride in 400 ml of anhydrous N,N-dimethylformamide was stirred at room temperature for 50 minutes. The reaction mixture was poured into 1.5 l of ice cold water and the aqueous phase was extracted four times with 200 ml of ether. The organic phase was washed twice with water, aqueous sodium chloride solution, dried with magnesium sulfate and concentrated in vacuo to a white foam. The crude product was purified by silica gel column chromatography, with a methylene chloride:ethyl acetate, 90:10 to 70:30 solvent system to give 46.5 g of 5-O-t-butyldimethylsilyl avermectin B1a/B1b as an amorphous foam, which was characterized by its $^1$H-NMR and mass spectra.

EXAMPLE 2

5-O-t-Butyldimethylsilyl-4"-oxo avermectin B1a/B1b

To a solution containing 9.1 ml of oxalyl; chloride in 230 ml of dry methylene chloride stirred at –60° C., was added 15 ml of dry dimethylsulfoxide dissolved in 120 ml of dry methylene chloride during 15 min. Then a solution of 46.5 g of 4-O-t-butyldimethylsilyl avermectin B1a/B1b dissolved in 230 ml of dry methylene chloride was added over a period of 15 minutes while maintaining the temperature at –60° C. The reaction mixture was stirred at this temperature for 30 minutes when 65 ml of dry triethylamine was added. The mixture was stirred for 5 additional minutes at –60° C., the cooling bath was removed and the reaction mixture was allowed to come to ambient temperature. After addition of water the reaction product was extracted with methylene chloride, the extract was washed with water, dried and concentrated in vacuo to 45.5 g of a yellow foam. This was identified by its mass and NMR spectra as 5-O-t-butyldimethylsilyl-4"-oxo avermectin B1a/B1b, which was used for further chemical reactions without purification.

EXAMPLE 3

4"-Deoxy-4"-epi-methylamino-5-O-t-butyldimethylsilyl avermectin B1a/B1b and

4"-deoxy-4"-methylamino-5-O-t-butyldimethylsilyl avermectin B1a/B1b

A solution of 26 ml of glacial acetic acid in 300 ml of methanol was treated with methylamine gas at 0° C., until the pH of the solution reached 9.0. To this a solution containing 44.5 g of 5-O-t-butyldimethylsilyl-4"-oxo avermectin B1a/B1b in 200 ml of methanol was added, and the reaction mixture was stirred at room temperature for 1 hour, when a solution of 3.5 g of sodium cyanobrohydride in 75 ml of methanol was added dropwise over 10 minutes. After 50 minutes the reaction mixture was poured into 1.5 l of cold aqueous sodium carbonate solution and the product was extracted with ether. The extract was washed with water, dried, and concentrated in vacuo to 44.8 g of yellow foam. Thin layer chromatography (silica gel, ethyl acetate: methylene chloride, 85:15) of the crude product at this point shows several spots. Further purification by silica gel column chromatography using ethyl acetate solvent mixtures gave 4.7 g of 5-O-t-butyldimethylsilyl-4"-epi avermectin B1a/B1b, 1.2 g of 4"-deoxy-4"-methylamino-5-O-t-butyldimethylsilyl avermectin B1a/B1b, and 14 g of 4"-deoxy-4"-epi-methylamino-5-O-t-butyldimethylsilyl avermectin B1a/B1b as light foams, which were characterized by their mass spectrum and their $^1$H-NMR, and $^{13}$C-NMR spectra.

EXAMPLE 4

4"-Deoxy-4"-epi-methylamino avermectin B1a/B1b

A solution of 14 g of 4"-deoxy-4"-epi-methylamino-5-O-t-butyldimethylsilyl avermectin B1a/B1b in 200 ml of methanol and a solution of 7 g of p-toluenesulfonic acid monohydrate in 500 ml of methanol was mixed and stirred at room temperature for 45 minutes, and then poured into dilute aqueous sodium carbonate solution. The product was extracted with ethyl acetate, washed with water and dried over magnesium sulfate, concentrated in vacuo, and purified by preparative silica gel column chromatography with a methylene chloride/methanol 95:5 solvent mixture to give 6.7 g of 4"-deoxy-4"-epi-methylamino avermectin B1a/B1b, which was identified by NMR and mass spectra.

EXAMPLE 5

4"-Deoxy-4"-epi-methylamino avermectin B1b/B1a Benzoic Acid Salt (Type A material)

4"-Deoxy-4"-epi-methylamino avermectin B1a/B1b (5.10 kg, 5.75 m) in methyl tert-butyl ether (18 L) was treated with benzoic acid (7.55 g, 6.18 m) at 25° C. To this solution was added hexanes (36 L) over a 0.5–1.0 hour period, whereupon crystallization occurs during the addition. The crystalline slurry was cooled to 0°–2° C., aged for 1 hour at 0°–2° C., then filtered. The filter cake was then washed with a mixture of methyl tert-butyl ether/hexanes (1:2) and dried in vacuo at 60° C. to give 5.7 kg of 4"-deoxy-4"-epi-methylamino avermectin B1a/B1b benzoic acid salt (Type A).

Molecular Weight: 1008

Melting Point: 133°–136° C.

Microanalysis: calculated: C, 66.71; H, 8.10; N, 1.39 found: C, 66.93; H, 8.32; N, 1.20.

EXAMPLE 6

| Preparation of Type B Product | |
|---|---|
| Materials | Amounts |
| TYPE A MATERIAL (obtained by crystallization from MTBE as described in Example 5) | 3.59 Kg 94.2 wt %<br>2.33 Kg 95.7 wt %<br>5.92 Kg (5.61 Kg by assay) |
| ACETONITRILE (HPLC GRADE) | 40 L (KF = 0.2 mg/ml) |
| WATER (DI) | 570 mL |

Procedure

A 50 L 4-neck round bottom flask was equipped with a mechanical stirrer, $N_2$ inlet, thermocouple and funnel. After purging the vessel with $N_2$, acetonitrile (12 L, KF=0.2 mg/ml) was added and warmed to 50–55° C., and Type A material was charged. Upon complete addition (30 minute), the mixture was aged an additional 10 minutes in a nitrogen atmosphere to give a clear red-brown solution.

The batch was diluted with additional acetonitrile (6 L), water (270 mL) was added, and then seed crystals of form Type B (10 g) were added at 45° C. Crystal growth began immediately and rapidly at 45° C. Crystallization must initiate, and largely occur at >35° C. to assure formation of Type B crystals.

The batch was cooled to 20° C. over a 45 minutes period and aged for 2.5 hrs. The crystalline slurry thickened during this period and made stirring difficult. Additional acetonitrile (2 L) was added, and the slurry was cooled to 5° C. over 1 hr. After aging at 5° C. for 30 minute the slurry was filtered onto a 22-in. diameter Cenco-Lapp funnel lined with paper and polypropylene. The mother liquor was recycled back to the crystallization vessel to rinse and transfer the remaining product. The cake was washed with cold (2° C.) wet acetonitrile (5×4 L, each 1.5% (v/v) in water). The cake was partially dried with a stream of nitrogen passed through the cake for 30 minute and it was then transferred to the Hull dryer.

The cake was dried at 30° C. in vacuo (25 in.) over 3 days to a constant weight and an acetonitrile content <0.1 wt % by GC. The batch product was 4.95 Kg of Type B material.

| Analyses B1a anhydrous Type B | | |
|---|---|---|
| MW | 1008.26 | |
| FORMULA | $C_{56}H_{81}NO_{15}$ | |
| CFA: | OFF-WHITE POWDER | |
| X-RAY | CRYST. TYPE B HEMIHYDRATE | |
| HPLC* | 97.1 WT %<br>97.8 area % | |
| TLC | SINGLE SPOT | |
| TITRATION* | 100% (Perchloric acid) | |
| UV* | A % 333, 245 nm in methanol | |
| KF | 1.08 wt % | |
| GC | $CH_3CN$ | <0.01% |
| | HEXANES | <0.01% |
| | MTBE | nd, <0.01% |
| | IPAc | nd, <0.01% |

*corrected for KF, GC

What is claimed is:

1. A crystalline compound 4"-deoxy-4"-epi-methylamino avermectin B1a/B1b, benzoic acid salt, hemihydrate Type B in substantially pure form.

2. The crystalline compound of claim 1 which is 4"-deoxy-4"-epi-methylamino avermectin B1a/B1b, benzoic acid salt, hemihydrate in substantially pure form characterized in that differential scanning calorimetry at a heating rate of 20° C. per minute characterizes a water loss endothern with a peak temperature of 74° C. and a melting/decomposition endothern with a peak temperature of 155° C. and an extrapolated onset temperature of 150° C. and an associated heat of 56 Joules per gram; an X-ray powder diffraction characterized by d-spacings of 18.13, 9.08, 8.58, 5.03, 4.61, 4.53, 3.97 and 3.82 Å; and in pH5 acetate buffer a solubility of 0.32 mg per ml.

3. A method for the control of agricultural insects, which comprises applying to an area infested with such agricultural insects an effective amount of the stable salt of claim 1.

4. A composition useful for the treatment of insect infestations of plants or plant products which comprises an inert carrier and an effective amount of the stable salt of claim 1.

* * * * *